United States Patent [19]

Rentzea et al.

[11] Patent Number: 4,599,335
[45] Date of Patent: Jul. 8, 1986

[54] DIAMINE DERIVATIVES, COMPOSITIONS AND USE

[75] Inventors: Costin Rentzea, Heidelberg; Ernst Buschmann, Ludwigshafen; Norbert Meyer, Ladenburg; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 761,339

[22] Filed: Jul. 31, 1985

Related U.S. Application Data

[63] Continuation of Ser. No. 492,341, May 6, 1983, abandoned.

[51] Int. Cl.$^4$ ............... A01N 33/12; A01N 43/60; C07C 87/46; C07D 295/02
[52] U.S. Cl. ................... 514/255; 514/643; 544/399; 544/401; 544/402; 544/403; 564/282; 564/285; 564/287; 564/288; 564/289
[58] Field of Search ............... 544/399, 401, 402, 403; 564/282, 285, 287, 288, 289; 514/255, 643

[56] References Cited

U.S. PATENT DOCUMENTS

| | | | |
|---|---|---|---|
| 3,055,939 | 9/1962 | Cavallito et al. | 564/289 |
| 3,322,768 | 5/1967 | Schorr et al. | 544/403 |
| 4,301,284 | 11/1981 | Buschmann et al. | 544/178 |

FOREIGN PATENT DOCUMENTS

| | | |
|---|---|---|
| 836937 | 4/1952 | Fed. Rep. of Germany . |
| 1493745 | 5/1969 | Fed. Rep. of Germany . |
| 2727482 | 1/1979 | Fed. Rep. of Germany . |
| 1109502 | 4/1968 | United Kingdom . |

OTHER PUBLICATIONS

Chemical Week, Jun. 21st, 1972, p. 46.

Primary Examiner—Robert W. Ramsuer
Attorney, Agent, or Firm—Keil & Weinkauf

[57] ABSTRACT

Diamine derivatives of the formula

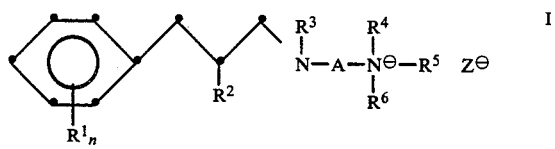

where $R^1$ is unsubstituted or substituted alkyl, unsubstituted or substituted aryl or aralkyl, bicycloalkyl, alkoxy, acyl or halogen, n is 0, 1, 2 or 3, $R^2$ is alkyl, alkenyl or alkoxy, A is unsubstituted or substituted alkylene or unsubstituted or substituted cycloalkylene, $R^3$, $R^4$ and $R^5$ are each unsubstituted or substituted alkyl, alkenyl, alkynyl or unsubstituted or substituted benzyl, or $R^3$ and $R^4$, together with A and the two nitrogen atoms bonded to A, form an unsubstituted or substituted piperazine or perhydrodiazepine ring, or $R^4$ and $R^5$, together with the nitrogen atom, form an unsubstituted or substituted heterocyclic ring, $R^6$ is alkyl, alkenyl, alkynyl or unsubstituted or substituted aralkyl or aryloxyalkyl, and Z is an anion of an acid, and fungicides containing these compounds.

9 Claims, No Drawings

DIAMINE DERIVATIVES, COMPOSITIONS AND USE

This application is a continuation of application Ser. No. 492,341, filed on May 6, 1983, now abandoned.

The present invention relates to novel diamine derivatives, a process for their preparation, and fungicides containing these compounds as active ingredients.

It has been disclosed that N-trichloromethylthiotetrahydrophthalimide can be used as a fungicide (*Chemical Week*, June 21, 1972, page 46).

We have found that diamine derivatives of the formula

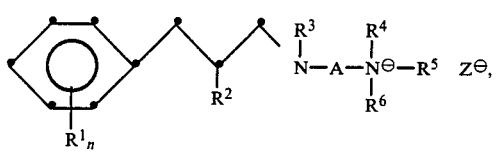

where $R^1$ is unsubstituted or halogen-substituted alkyl, unsubstituted or substituted aryl or aralkyl, cycloalkyl, bicycloalkyl, alkoxy, acyl or halogen, n is 0, 1, 2 or 3, $R^2$ is alkyl, alkenyl or alkoxy, A is $C_2$-$C_4$-alkylene which is unsubstituted or substituted by alkyl, haloalkyl, alkoxy or halogen, or is $C_5$-$C_7$-cycloalkylene which is unsubstituted or substituted by alkyl, haloalkyl or alkoxy, $R^3$, $R^4$ and $R^5$ independently of one another are each unsubstituted or halogen-substituted alkyl, alkenyl, alkynyl, or benzyl which is unsubstituted or substituted by halogen, alkyl, alkoxy, trifluoromethyl, cyano or nitro, or $R^3$ and $R^4$, together with A and the two nitrogen atoms which are bonded to A, form an unsubstituted or alkyl-substituted piperazine or perhydrodiazepine ring, or $R^4$ and $R^5$, together with the nitrogen atom of which they are substituents, form an unsubstituted or alkyl-substituted 5-membered, 6-membered or 7-membered heterocyclic ring containing 1 or 2 hetero atoms, $R^6$ is alkyl, alkenyl, alkynyl or unsubstituted or substituted aralkyl or aryloxyalkyl, and Z is an anion of any non-phytotoxic acid, have a good action against fungi and bacteria.

$R^1$ is, for example, hydrogen, fluorine, chlorine, bromine, $C_1$-$C_8$-alkyl, eg. methyl, ethyl, n-propyl, isopropyl, n-butyl, isobutyl, tert.-butyl, n-pentyl, tert.-amyl, 1,1-dimethylbutyl, 1,1-dimethylpentyl, 1,1-dimethylhexyl, 1,1-diethylpropyl or 1,1,2-trimethylpropyl, halo-$C_1$-$C_4$-alkyl, eg. 2-chloro-1,1-dimethylethyl or trifluoromethyl, cyclohexyl, phenyl, halophenyl, eg. 4-chlorophenyl, benzyl, halobenzyl, eg. 4-chlorobenzyl, phenylethyl, $C_1$- or $C_2$-alkoxy, eg. methoxy or ethoxy, or $C_1$- or $C_2$-alkylcarbonyl, eg. acetyl, propionyl or benzoyl.

$R^2$ is, for example, methyl, ethyl, propyl, butyl, allyl or crotyl.

A is, for example, —(CH$_2$)$_2$—, —(CH$_2$)$_3$-,

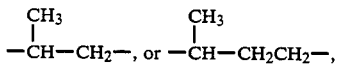

preferably 1,2-, 1,3- or 1,4-cyclohexylene

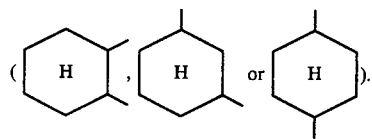

$R^3$ is, for example, methyl or ethyl.

$R^4$ and $R^5$ are each, for example, methyl, ethyl, propyl, allyl, butenyl, propargyl, benzyl, halobenzyl, eg. 4-fluorobenzyl, 4-chlorobenzyl, 3-chlorobenzyl, 4-bromobenzyl, 3,4-dichlorobenzyl or 2,4-dichlorobenzyl, or 3-trifluoromethylbenzyl, 4-trifluoromethylbenzyl, 4-methylbenzyl, 4-(tert.-butyl)-benzyl, 4-methoxybenzyl, 4-cyanobenzyl or 4-nitrobenzyl.

Preferred compounds of the formula I are those in which $R^3$ and $R^4$, together with A and the two nitrogen atoms, form a piperazine or perhydrodiazepine ring, or those in which $R^4$ and $R^5$, together with N, form an unsubstituted or methyl-substituted pyrrolidine, piperidine or morpholine ring.

$R^6$ is, for example, methyl, ethyl, propyl, butyl, isobutyl, pentyl, allyl, but-2-en-1-yl, 4-chlorobut-2-en-1-yl, propargyl, naphth-1-ylmethyl, naphth-2-ylmethyl, unsubstituted or substituted benzyl, eg. 2-fluorobenzyl, 4-fluorobenzyl, 2-chlorobenzyl, 3-chlorobenzyl, 4-chlorobenzyl, 3-bromobenzyl, 4-bromobenzyl, 3-trifluoromethylbenzyl, 4-trifluoromethylbenzyl, 3-methylbenzyl, 4-methylbenzyl, 4-tert.-butylbenzyl, 4-cyanobenzyl, 4-nitrobenzyl, 2,4-dichlorobenzyl, 3,4-dichlorobenzyl, 2,4-dimethylbenzyl, 4-methoxybenzyl or 2,3,6-trichlorobenzyl, or 1-(4-tert.-butylphenyl)-2-methylprop-3-yl, 1-phenoxyeth-2-yl, 1-phenoxyprop-3-yl, 1-(3-chlorophenoxy)-eth-2-yl, 1-(4-chlorophenoxy)-eth-2-yl, 1-(4-methylphenoxy)-eth-2-yl, 1-(4-methoxyphenoxy)-eth-2-yl, 1-(4-nitrophenoxy)-prop-3-yl, 1-(4-trifluoromethylphenoxy)-eth-2-yl or 1-phenoxybut-4-yl. Z is, for example, methylsulfonate, p-dodecylbenzenesulfonate, sulfate, methosulfate, nitrate, phosphate, iodide, or in particular chloride or bromide.

The novel diamine derivatives of the formula I possess a chiral carbon atom attached to the ligand $R^2$, and, depending on the nature of $R^1$, $R^3$, $R^4$, $R^5$, $R^6$ and A, may possess further chiral centers in these radicals. The optically pure enantiomers or the diastereomers can be obtained by a conventional method. The present invention also embraces these compounds in pure form and in the form of mixtures. Both the pure enantiomers or the diastereomer pairs and the mixtures obtained in the synthesis are active as fungicides.

The diamine derivatives of the formula I are obtained, for example, by a process wherein a compound of the formula

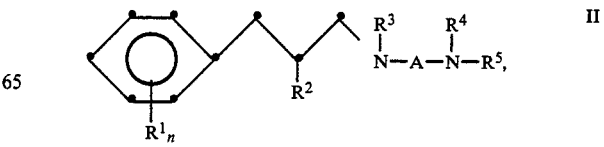

where A, $R^1$, $R^2$, $R^3$, $R^4$, $R^5$ and n have the above meanings, is reacted with a compound $R^6Z$, where $R^6$ and Z have the above meanings.

The reaction is carried out in the presence or absence of a solvnt or diluent, at from 20° to 150° C., preferably from 30° to 140° C. The reaction is advantageously carried out using equimolar amounts of the starting material of the formula II and the compound $R^6Z$.

Examples of preferred solvents or diluents which are inert to the reactants are aliphatic or aromatic hydrocarbons or aliphatic or aromatic halohydrocarbons, such as pentane, cyclohexane, benzene, toluene, xylenes and chlorobenzene, aliphatic ketones, such as acetone, methyl ethyl ketone, diethyl ketone and cyclopentanone, ethers, such as diethyl ether, dimethoxyethane, methyl tert.-butyl ether, tetrahydrofuran and dioxane, esters, such as ethyl acetate, nitriles, such as acetonitrile, amides, such as dimethylformamide, dimethylacetamide and N-methylpyrrolidone, and mixtures of these solvents.

The preparation of the starting compounds of the formula II by a conventional process is described together with the synthesis of the novel compounds of the formula I.

Examples of suitable quaternizing agents of the formula $R^6Z$, in addition to the alkyl, alkenyl, alkynyl, benzyl and aralkyl halides, are dimethyl sulfate, diethyl sulfate and sulfonates of the formula $R-SO_3-R^6$, where $R^6$ is $C_1-C_7$-alkyl or is aralkyl or phenyl which is substituted by halogen or alkyl.

The Examples which follow illustrate the preparation of the compounds of the formula I.

EXAMPLE 1

(a) 274 g of trans-1,2-diaminocyclohexane and 134.4 g of 3-(4-tert.-butylphenyl)-2-methylpropyl chloride (German Laid-Open Application DOS No. 2,752,096) were stirred for 10 hours at 140° C. and then cooled to +10° C. in an ice bath, and 200 ml of a 50% strength by weight sodium hydroxide solution were added slowly, followed by the addition of 200 ml of ether. The organic phase was separated off, dried over potassium hydroxide and distilled to give 151 g of N-(3-(4-tert.-butylphenyl)-2-methylpropyl)-trans-1,2-diaminocyclohexane of boiling point 175°–180° C./0.3 mbar. Yield: 83.3% of theory.

Using the above method, 274 g of a mixture of 70% of trans-1,2-diaminocyclohexane and 30% of cis-1,2-diaminocyclohexane gave 154.1 g of N-(3-(4-tert.-butylphenyl)-2-methylpropyl)-1,2-diaminocyclohexane as a cis/trans mixture of boiling point 175°–185° C./0.3 mbar.

Yield: 85% of theory.

(b) 151 g of N-(3-(4-tert.-butylphenyl)-2-methylpropyl)-trans-1,2-diaminocyclohexane were added dropwise in the course of 30 minutes to a mixture of 260 ml of 98% strength formic acid and 400 ml of 40% strength aqueous formaldehyde solution, at from 50° to 80° C. The mixture was stirred for 10 hours at from 90° to 95° C. and then cooled to +10° C., 234 ml of 36% strength hydrochloric acid were added carefully, and the mixture was then evaporated down under reduced pressure. The residue was stirred with 940 ml of 30% strength sodium hydroxide solution, and the mixture was extracted by shaking with three times 150 ml of ether. The ether extract was dried over potassium hydroxide and distilled to give 132 g of N',N'',N''-trimethyl-N'-(3-(4-tert.-butylphenyl)-2-methylpropyl)-1,2-diaminocyclohexane of boiling point 180°–190° C./0.3 mbar and $n_D^{25}=1.5097$. Yield: 76.5% of theory.

(c) 9.2 g of 4-tert.-butylbenzyl chloride were added to a solution of 10.5 g of N',N'',N''-trimethyl-N'-(3-(4-tert.-butylphenyl)-2-methylpropyl)-1,2-diaminocyclohexane in 10 ml of dioxane and 45 ml of acetonitrile, and the mixture was stirred for 16 hours at 80° C. and then evaporated down under reduced pressure. The residue was washed with three times 20 ml of ether and was dried for 3 hours at 80° C. under a pressure of 0.2 mbar. 11 g of N'-[N''-(3-(4-tert.-butylphenyl)-2-methylpropyl)-N''-methylaminocyclohexyl]-N',N'-dimethyl-N'-(4-tert.-butylbenzyl)-ammonium chloride were obtained as a pale yellow resin (compound 1). Yield: 68.7% of theory.

IR spectrum (film): 3,022, 2,964, 2,866, 1,512, 1,476, 1,463, 1,364, 1,270, 1,110, 1,030, 843 and 563 cm$^{-1}$.

EXAMPLE 2

(a) 57 g of trans-1,2-diaminocyclohexane, 208 g of 3-(4-tert.-butylphenyl)-2-methylpropanal and 3 ml of acetic acid in 300 ml of toluene were refluxed for 5 hours until 18 ml of an azeotropic mixture of water and toluene had distilled off. The toluene was then distilled off under reduced pressure, and the residue was directly reacted further to give 223 g of the Schiff base

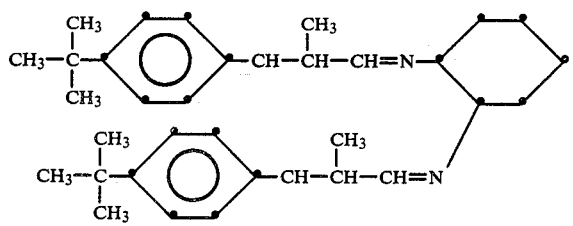

Yield: 91.7% of theory.

(b) 200 g of the Schiff base were dissolved in 500 ml of methanol, 38 g of sodium borohydride were added, a little at a time, at 0° C., and the mixture was stirred for 12 hours at 20° C. Thereafter, the methanol was distilled off, the residue was dissolved in 500 ml of methylene chloride, the solution was stirred for 1 hour with 300 ml of 25% strength potassium hydroxide solution, the organic phase was separated off, washed with twice 200 ml of water and dried over sodium sulfate, and the methylene chloride was distilled off under reduced pressure. The residue comprised 195 g of N',N''-bis-[3-(4-tert.-butylphenyl)-2-methylpropyl]-1,2-diaminocyclohexane in the form of a pale brown resin. Yield: 97.5% of theory.

(c) 200 g of N',N''-bis-[3-(4-tert.-butylphenyl)-2-methylpropyl]-1,2-diaminocyclohexane were added, a little at a time, to a mixture of 134 ml of a 40% strength aqueous formaldehyde solution and 86.6 ml of 98% strength formic acid, at from 50° to 80° C. The mixture was stirred for 10 hours at 95° C. and then cooled to +10° C., 234 ml of 36% strength hydrochloric acid were added carefully and the mixture was then evaporated down under reduced pressure. The residue was stirred with 940 ml of 30% strength sodium hydroxide solution and extracted by shaking with four times 150 ml of ether. The ether extract was washed with twice 100 ml of water, dried over potassium hydroxide and then concentrated for 3 hours at 100° C. under a pressure of 0.2 mbar. 185.4 g of N',N"-dimethyl-N',N"-bis-[3-(4-tert.-butylphenyl)-2-methylpropyl]-1,2-diaminocyclohexane were obtained in the form of a pale brown resin. Yield: 87.7% of theory.

(d) 7.2 g of benzyl bromide were added to a solution of 10.9 g of N',N"-bis-[3-(4-tert.-butylphenyl)-2-methylpropyl]-1,2-diaminocyclohexane in 20 ml of dioxane and 30 ml of acetonitrile, and the mixture was stirred for 3 days at 70° C. and then evaporated down under reduced pressure. The residue was washed three times with petroleum ether and finally dried for 4 hours at 100° C. under a pressure of 0.2 mbar. 6.6 g of N'-[N"-methyl-N"-(3-(4-tert.-butylphenyl)-2-methylpropyl)-aminocyclohexyl]-N'-methyl-N'-benzyl-N'-(3-(4-tert.-butylphenyl)-2-methylpropyl)-ammonium bromide were obtained in the form of a pale brown resin (compound 2). Yield: 45.6% of theory.

IR spectrum (film): 3,030, 2,962, 2,866, 1,515, 1,460, 1,393, 1,364, 1,269, 1,204, 1,109, 853 and 706 cm$^{-1}$.

EXAMPLE 3

(a) 533 g of 3-(4-tert.butylphenyl)-2-methylpropyl chloride and 714 g of 4-methylpiperazine were stirred for 7 hours at 140° C. and then cooled to +10° C. in an ice bath, and 400 ml of 50% strength sodium hyroxide solution were added slowly, followed by the addition of 500 ml of ether. The organic phase was separated off, dried over sodium hydroxide and distilled to give 640 g of 1-methyl-4-[3-(4-tert.-butylphenyl)-2-methylpropyl]-piperazine of boiling point 135°-140° C./0.3 mbar.

(b) A solution of 14.4 g of 1-methyl-4-[3-(4-tert.-butylphenyl)-2-methylpropyl]-piperazine and 10.3 g of benzyl bromide in 200 ml of ethyl acetate was refluxed for 6 hours, after which the mixture was evaporated down to 80 ml and then cooled to +5° C. The precipitated product was filtered off under suction, washed with ether and dried. 18.4 g of 1-methyl-1-benzyl-4-[3-(4-tert.-butylphenyl)-2-methylpropyl]-piperazinium bromide were obtained in the form of colorless crystals of melting point 216° C. (compound 3).

The compounds below were prepared by a similar procedure.

| No. | $R^1$ | $R^2$ | $R^3$ | A | $R^4$ | $R^5$ | $R^6$ | Z | Physical constant or infrared spectrum [cm$^{-1}$] (film) |
|---|---|---|---|---|---|---|---|---|---|
| 4 | 4-C(CH$_3$)$_3$ | —CH$_3$ | —CH$_3$ | —(CH$_2$)$_2$— | —CH$_3$ | —CH$_3$ | 2,4-Cl$_2$C$_6$H$_3$—CH$_2$— | Cl | 3002, 2963, 1589, 1475, 1384, 1105, 1055, 869, 849, 786 |
| 5 | 4-C(CH$_3$)$_3$ | —CH$_3$ | —CH$_3$ | —(CH$_2$)$_2$— | —CH$_3$ | —CH$_3$ | 3,4-Cl$_2$C$_6$H$_3$—CH$_2$— | Cl | 2962, 1471, 1219, 1136, 1035, 826, 672 |
| 6 | 4-C(CH$_3$)$_3$ | —CH$_3$ | —CH$_3$ | —(CH$_2$)$_3$— | —CH$_3$ | —CH$_3$ | 4-(tert.-C$_4$H$_9$)C$_6$H$_4$—CH$_2$— | Cl | m.p. 201–207° C. |
| 7 | 4-C(CH$_3$)$_3$ | —CH$_3$ | —CH$_3$ | —(CH$_2$)$_3$— | —CH$_3$ | —CH$_3$ | 4-ClC$_6$H$_4$—CH$_2$— | Cl | 2963, 1599, 1493, 1414, 1270, 1216, 1093, 1017, 852, 818 |
| 8 | 4-C(CH$_3$)$_3$ | —CH$_3$ | —CH$_3$ | —(CH$_2$)$_3$— | —CH$_3$ | —CH$_3$ | 2,4-Cl$_2$C$_6$H$_3$—CH$_2$— | Cl | 3010, 2963, 2869, 1589, 1475, 1384, 1107, 868, 827 |
| 9 | 4-C(CH$_3$)$_3$ | —CH$_3$ | —CH$_3$ | 1,2-cyclohexylene | —CH$_3$ | —CH$_3$ | allyl | Br | resin |
| 10 | 4-C(CH$_3$)$_3$ | —CH$_3$ | —CH$_3$ | 1,2-cyclohexylene | —CH$_3$ | —CH$_3$ | but-2-en-1-yl | Br | resin |
| 11 | 4-C(CH$_3$)$_3$ | —CH$_3$ | —CH$_3$ | 1,2-cyclohexylene | —CH$_3$ | —CH$_3$ | propargyl | Br | resin |
| 12 | 4-C(CH$_3$)$_3$ | —CH$_3$ | —CH$_3$ | 1,2-cyclohexylene | —CH$_3$ | —CH$_3$ | Cl—CH$_2$—CH=CH—CH$_2$ | Cl | resin |
| 13 | 4-C(CH$_3$)$_3$ | —CH$_3$ | —CH$_3$ | 1,2-cyclohexylene | —CH$_3$ | —CH$_3$ | C$_6$H$_5$—CH$_2$— | Br | 2963, 2864, 1510, 1375, 1220, 1027, 850, 735, 578 |
| 14 | 4-C(CH$_3$)$_3$ | —CH$_3$ | —CH$_3$ | 1,2-cyclohexylene | —CH$_3$ | —CH$_3$ | 4-ClC$_6$H$_4$—CH$_2$ | Cl | 3014, 2963, 2862, 1512, 1490, 1377, 1090, 1030, 1015, 855 |
| 15 | 4-C(CH$_3$)$_3$ | —CH$_3$ | —CH$_3$ | 1,2-cyclohexylene | —CH$_3$ | —CH$_3$ | 2,4-Cl$_2$C$_6$H$_3$—CH$_2$— | Cl | 3020, 2964, 2865, 1588, 1510, 1475, 1382, 1102, 864, 842 |
| 16 | 4-C(CH$_3$)$_3$ | —CH$_3$ | —CH$_3$ | 1,2-cyclohexylene | —CH$_3$ | —CH$_3$ | 1-C$_{10}$H$_7$—CH$_2$— | Cl | 3022, 2958, 2868, 1514, 1461, 1362, 1270, 1110, 1030, 810, 784 |
| 17 | 4-C(CH$_3$)$_3$ | —CH$_3$ | —CH$_3$ | 1,2-cyclohexylene | —CH$_3$ | —CH$_3$ | C$_6$H$_5$—CH=CH—CH$_2$ | Br | 2954, 2866, 1450, 1365, 1270, 1031, 986, 850, 758, 695, 575 |
| 18 | 4-C(CH$_3$)$_3$ | —CH$_3$ | —CH$_3$ | 1,2-cyclohexylene | —CH$_3$ | —CH$_3$ | 4-FC$_6$H$_4$—CH$_2$— | Cl | 2960, 2867, 1607, 1513, 1476, 1462, 1229, 1030, 865, 845 |
| 19 | 4-C(CH$_3$)$_3$ | —CH$_3$ | —CH$_3$ | 1,2-cyclohexylene | —CH$_3$ | —CH$_3$ | 4-(NO$_2$)C$_6$H$_4$—CH$_2$— | Br | 2961, 2865, 1607, 1525, 1476, 1463, 1347, 1109, 842, 738 |
| 20 | 4-C(CH$_3$)$_3$ | —CH$_3$ | —CH$_3$ | 1,2-cyclohexylene | —CH$_3$ | —CH$_3$ | 2,4-(CH$_3$)$_2$C$_6$H$_3$—CH$_2$— | Cl | 3020, 2960, 2920, |

| | | | | | |
|---|---|---|---|---|---|
| | | | | hexylene | 2854, 1507, 1457, 1437, 1385, 1270, 1110, 830 |
| 21 | 4-C(CH₃)₃ | —CH₃ | —CH₃ | 1,2-cyclohexylene | 4-BrC₆H₄—CH₂— | Br | 2953, 2865, 1488, 1461, 1364, 1072, 1013, 851, 844, 800 |
| 22 | 4-C(CH₃)₃ | —CH₃ | —CH₃ | 1,2-cyclohexylene | 3-(CF₃)C₆H₄—CH₂— | Cl | 2963, 1468, 1331, 1206, 1168, 1126, 1077, 1030, 815, 710 |
| 23 | 4-C(CH₃)₃ | —CH₃ | —CH₃ | 1,2-cyclohexylene | 4-(CH₃)C₆H₄—CH₂— | Cl | 2962, 2865, 1516, 1476, 1462, 1364, 1270, 1110, 1029, 825 |
| 24 | 4-C(CH₃)₃ | —CH₃ | —CH₃ | 1,2-cyclohexylene | C₆H₅—O—CH₂—CH₂— | Br | 2961, 1600, 1498, 1459, 1365, 1239, 1048, 1030, 850, 755 |
| 25 | 4-C(CH₃)₃ | —CH₃ | —CH₃ | 1,2-cyclohexylene | 3-ClC₆H₄—O—(CH₂)₂— | Br | 2959, 1595, 1476, 1284, 1230, 1047, 1030, 975, 850, 775 |
| 26 | 4-C(CH₃)₃ | —CH₃ | —CH₃ | 1,2-cyclohexylene | C₆H₅—CH₂ | Br | 2963, 2932, 2864, 1511, 1458, 1377, 1220, 1029, 851, 705 |
| 27 | 4-C(CH₃)₂C₂H₅ | —CH₃ | —CH₃ | 1,2-cyclohexylene | 4-(tert.-C₄H₉)C₆H₄—CH₂— | Cl | 2964, 2929, 2866, 1513, 1462, 1363, 1270, 1110, 863, 843 |
| 28 | 4-C(CH₃)₂C₂H₅ | —CH₃ | —CH₃ | 1,2-cyclohexylene | 2,4-Cl₂C₆H₃—CH₂— | Cl | 2964, 2866, 1588, 1511, 1475, 1384, 1102, 1053, 1030, 865 |
| 29 | 4-C(CH₃)₂C₂H₅ | —CH₃ | —CH₃ | 1,2-cyclohexylene | 4-ClC₆H₄—CH₂ | Cl | 2963, 2864, 1492, 1462, 1377, 1093, 1017, 854, 808, 776 |
| 30 | 4-C(CH₃)₃ | —CH₃ | n-C₃H₇ | 1,2-cyclohexylene | 4-(tert.-C₄H₉)C₆H₄—CH₂—CH₂—CH—CH₂<br>　　　　　　　　　　　　　　　　　　　｜<br>　　　　　　　　　　　　　　　　　　　CH₃ | Br | 2963, 2867, 1512, 1462, 1364, 1269, 1110, 1050, 853 |
| 31 | 4-C(CH₃)₃ | —CH₃ | CH₂=CH—CH₂— | 1,2-cyclohexylene | " | Br | 2963, 2868, 1512, 1462, 1364, 1268, 1109, 1020, 852, 826 |
| 32 | 4-C(CH₃)₃ | —CH₃ | 4-ClC₆H₄—CH₂— | 1,2-cyclohexylene | " | Cl | 2963, 2867, 1512, 1462, 1364, 1269, 1110, 1094, 843, 810 |
| 33 | 4-C(CH₃)₃ | —CH₃ | 2,4-Cl₂C₆H₃—CH₂ | 1,2-cyclohexylene | " | Cl | 2962, 2867, 1512, 1385, 1364, 1269, 1200, 1109, 1052, 850 |
| 34 | 4-C(CH₃)₃ | —CH₃ | 3,4-Cl₂C₆H₃—CH₂ | 1,2-cyclohexylene | " | Cl | 2961, 1512, 1473, 1364, 1269, 1109, 1030, 840, 822 |
| 35 | 4-C(CH₃)₃ | —CH₃ | 4-(tert.-C₄H₉)C₆H₄—CH₂— | 1,2-cyclohexylene | " | Cl | 2963, 1513, 1462, 1364, 1269, 1123, 1109, 1020, 845 |
| 36 | 4-C(CH₃)₃ | —CH₃ | —CH₃ | 1,4-cyclohexylene | 4-ClC₆H₄—CH₂— | Br | m.p. 160-165° C. |
| 37 | 4-C(CH₃)₃ | —CH₃ | —CH₃ | 1,4-cyclohexylene | 2,4-Cl₂C₆H₃—CH₂— | Cl | m.p. 152-155° C. |

-continued

| No. | R¹ | R² | R³ + R⁴ | A | R⁵ | R⁶ | Z | Physical constant or infrared spectrum [cm⁻¹] (film) |
|---|---|---|---|---|---|---|---|---|
| 38 | 4-C(CH₃)₃ | —CH₃ | —C₂H₄— | 1,4-cyclo-hexylene | —CH₃ | —CH₃ | allyl | Br | m.p. 132–136° C. |
| 39 | 4-C(CH₃)₃ | —CH₃ | —C₂H₄— | 1,4-cyclo-hexylene | —CH₃ | —CH₃ | 4-CH₃—C₆H₄—CH₂— | Cl | m.p. 161–164° C. |
| 40 | 4-C(CH₃)₃ | —CH₃ | —C₂H₄— | 1,4-cyclo-hexylene | —CH₃ | —CH₃ | 4-(tert.-C₄H₉(C₆H₄)CH₂— | Br | m.p. 184–190° C. |
| 41 | 4-C(CH₃)₃ | —CH₃ | —C₂H₄— | 1,4-cyclo-hexylene | —CH₃ | —CH₃ | —CH₃ | Br | m.p. 232–234° C. |
| 42 | 4-C(CH₃)₃ | —CH₃ | —C₂H₄— | 1,4-cyclo-hexylene | —CH₃ | —CH₃ | C₆H₅—CH₂— | Br | resin |
| 43 | 4-C(CH₃)₃ | —CH₃ | —C₂H₄— | 1,3-cyclo-hexylene | —CH₃ | —CH₃ | 4-ClC₆H₄—CH₂— | Cl | 3018, 2966, 1605, 1598, 1492, 1412, 1215, 1019, 854, 820 |
| 44 | 4-C(CH₃)₃ | —CH₃ | —C₂H₄— | 1,3-cyclo-hexylene | —CH₃ | —CH₃ | 2,4-Cl₂C₆H₃—CH₂— | Cl | 3012, 2962, 2868, 1587, 1475, 1390, 1105, 868, 825 |
| 45 | 4-C(CH₃)₃ | —CH₃ | —C₂H₄— | 1,4-cyclo-hexylene | —CH₃ | —CH₃ | n-C₅H₁₁ | I | resin |
| 46 | 4-C(CH₃)₃ | —CH₃ | —CH₂—CH(CH₃)— | | —CH₃ | —CH₃ | 4-ClC₆H₄—CH₂— | Br | m.p. 85–87° C. (decomposition) |
| 47 | 4-C(CH₃)₃ | —CH₃ | —CH₂—CH(CH₃)— | | —CH₃ | —CH₃ | C₆H₅—CH₂— | Br | m.p. 97–102° C. |
| 48 | 4-C(CH₃)₃ | —CH₃ | —CH₂—CH(CH₃)— | | —CH₃ | —CH₃ | Allyl | Br | resin |
| 49 | 4-C(CH₃)₃ | —CH₃ | —CH₂—CH(CH₃)— | | —CH₃ | —CH₃ | —CH₃ | Br | m.p. 189–192° C. |
| 50 | 4-C(CH₃)₃ | —CH₃ | —CH₂—CH(CH₃)— | | —CH₃ | —CH₃ | 4-(CH₃)C₆H₄—CH₂— | Cl | resin |
| 106 | 4-C(CH₃)₃ | —CH₃ | —C₃H₆— | | —CH₃ | | 4-Cl—C₆H₄—CH₂ | Cl | m.p. 100–102° C. |

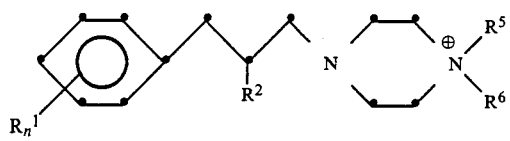

| No. | R¹ | R² | R⁵ | R⁶ | Z | M.p./°C. |
|-----|-----|-----|-----|-----|-----|-----|
| 51 | H | —CH₃ | —CH₃ | 4-ClC₆H₄—CH₂— | Cl | 206 |
| 52 | 4-CH₃—CO— | —CH₃ | —CH₃ | 4-ClC₆H₄—CH₂— | Cl | 186 |
| 53 | 4-C(CH₃)₃ | —CH₃ | —CH₃ | —CH₃ | Br | 230–232 |
| 54 | 4-C(CH₃)₃ | —CH₃ | —CH₃ | —CH₃ | I | 234 (decomposition) |
| 55 | 4-C(CH₃)₃ | —CH₃ | —CH₃ | allyl | Br | 146 |
| 56 | 4-C(CH₃)₃ | —CH₃ | —CH₃ | propargyl | Br | 215 |
| 57 | 4-C(CH₃)₃ | —CH₃ | —CH₃ | 4-ClC₆H₄—CH₂— | Cl | 216 |
| 58 | 4-C(CH₃)₃ | —CH₃ | —CH₃ | 4-ClC₆H₄—CH₂— | Br | 218 |
| 59 | 4-C(CH₃)₃ | —CH₃ | —CH₃ | 3-ClC₆H₄—CH₂— | Cl | 205 |
| 60 | 4-C(CH₃)₃ | —CH₃ | —CH₃ | 4-FC₆H₄—CH₂— | Cl | 211–212 |
| 61 | 4-C(CH₃)₃ | —CH₃ | —CH₃ | 4-(CN)C₆H₄—CH₂— | Cl | 223 |
| 62 | 4-C(CH₃)₃ | —CH₃ | —CH₃ | 4-(CH₃)C₆H₄—CH₂— | Cl | 216 |
| 63 | 4-C(CH₃)₃ | —CH₃ | —CH₃ | 4-(tert.-C₄H₉)C₆H₄—CH₂— | Cl | 217 |
| 64 | 4-C(CH₃)₃ | —CH₃ | —CH₃ | 3,4-Cl₂C₆H₃—CH₂— | Cl | 206 |
| 65 | 4-C(CH₃)₃ | —CH₃ | —CH₃ | 2,3,6-Cl₃C₆H₂—CH₂— | Cl | 91 |
| 66 | 4-C(CH₃)₃ | —CH₃ | propargyl | 4-ClC₆H₄—CH₂— | Br | 162 |
| 67 | 4-C(CH₃)₂C₂H₅ | —CH₃ | —CH₃ | 4-ClC₆H₄—CH₂— | Cl | 216 |
| 68 | 4-C(CH₃)₂C₃H₇—n-2-Cl | —CH₃ | —CH₃ | C₆H₅—CH₂— | Br | 211 |
| 69 | 4-C(CH₃)₂C₃H₇—n-2-Cl | —CH₃ | —CH₃ | 4-ClC₆H₄—CH₂— | Cl | 192 |
| 70 | 4-C(CH₃)₂C₃H₇—n-2-Cl | —CH₃ | —CH₃ | 4-(tert.-C₄H₉)C₆H₄—CH₂— | Cl | 204 |
| 71 | 4-C(CH₃)₂C₃H₇—i | —CH₃ | —CH₃ | —CH₃ | Br | 250 |
| 72 | 4-C(CH₃)₂C₃H₇—i | —CH₃ | —CH₃ | allyl | Br | 135 |
| 73 | 4-C(CH₃)₂C₃H₇—i | —CH₃ | —CH₃ | 4-ClC₆H₄—CH₂— | Br | 219 |
| 74 | 4-C(CH₃)₂C₃H₇—i | —CH₃ | —CH₃ | 4-(tert.-C₄H₉)C₆H₄—CH₂— | Br | 198 |
| 75 | 4-C(CH₃)₂C₄H₉—n | —CH₃ | —CH₃ | C₆H₅—CH₂— | Cl | 166 |
| 76 | 4-C(CH₃)₂C₄H₉—n | —CH₃ | —CH₃ | 4-ClC₆H₄—CH₂— | Cl | 194 |
| 77 | 4-C(CH₃)₂C₄H₉—n | —CH₃ | —CH₃ | 4-BrC₆H₄—CH₂— | Br | 199–201 |
| 78 | 4-C(CH₃)₂C₄H₉—n | —CH₃ | —CH₃ | 2,4-Cl₂C₆H₃—CH₂— | Cl | 176 |
| 79 | 2,4-Cl₂ | —C₃H₇—n | —CH₃ | —CH₃ | I | 175 |
| 80 | 2,4-Cl₂ | —C₃H₇—n | —CH₃ | allyl | Br | 193 |
| 81 | 2,4-Cl₂ | —C₃H₇—n | —CH₃ | C₆H₅—CH₂— | Br | 166 |
| 82 | 2,3,4-Cl₃ | —C₄H₉—n | —CH₃ | 4-ClC₆H₄—CH₂— | Cl | 150 |
| 83 | 2,3,4-Cl₃ | —C₄H₉—n | —CH₃ | 4-(tert.-C₄H₉)C₆H₄—CH₂— | Cl | 163 |
| 99 | 2,6-Cl₂ | —CH₃ | —CH₃ | 4-Cl—C₆H₄—CH₂ | Cl | 214–215 |
| | 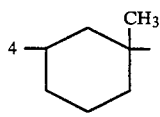 | | | | | |
| 100 | 4-cyclohexyl | —CH₃ | —CH₃ | 4-Cl—C₆H₄—CH₂ | Cl | 117–118 |
| 101 | 4-t-butyl | —CH₃ | —CH₃ | 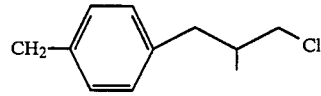 | Cl | 178–180 |
| 102 | 4-t-butyl | —CH₃ | —C₂H₅ | 4-Cl—C₆H₄—CH₂ | Cl | 164–166 |
| 103 | 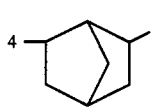 | —CH₃ | —CH₃ | 4-Cl—C₆H₄—CH₂ | Cl | 234–236 |
| 104 | 4-cyclohexyl | —CH₃ | —CH₃ | 4-tert.-butyl-C₆H₄—CH₂ | Cl | 188–190 |
| 105 | 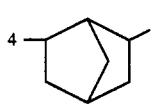 | —CH₃ | —CH₃ | 4-tert.-butyl-C₆H₄—CH₂ | Cl | 208–210 |

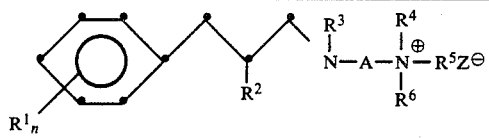

| No. | R¹ | R² | R³ | A | R⁴ + R⁵ | R⁶ | Z | M.p./°C |
|---|---|---|---|---|---|---|---|---|
| 84 | 4-C(CH₃)₃ | —CH₃ | —CH₃ | —(CH₂)₂— | —(CH₂)₄— | —CH₃ | Br | 120 |
| 85 | 4-C(CH₃)₃ | —CH₃ | —CH₃ | —(CH₂)₂— | —(CH₂)₄— | allyl | Br | resin |
| 86 | 4-C(CH₃)₃ | —CH₃ | —CH₃ | —(CH₂)₂— | —(CH₂)₅— | allyl | Br | resin |
| 87 | 4-C(CH₃)₃ | —CH₃ | —CH₃ | —CH₂CH₂CH(CH₃)— | —(CH₂)₅— | allyl | Br | resin |
| 88 | 4-C(CH₃)₃ | —CH₃ | —CH₃ | —(CH₂)₂— | —CH₂—CH₂—CH(CH₃)—CH₂—CH₂— | C₆H₅—CH₂ | Br | resin |
| 89 | H | —CH₃ | —CH₃ | —(CH₂)₂— | —CH₂—CH₂—O—CH₂—CH₂— | —CH₃ | Br | 185–188 |
| 90 | 4-C(CH₃)₃ | —CH₃ | —CH₃ | —(CH₂)₂— | —CH₂—CH₂—O—CH₂—CH₂— | but-2-en-1-yl | Br | 148–151 |
| 91 | H | —CH₃ | —CH₃ | —(CH₂)₂— | —CH₂—CH₂—O—CH₂—CH₂— | C₆H₅—CH₂— | Br | 125–128 |
| 92 | 4-C(CH₃)₃ | —CH₃ | —CH₃ | —(CH₂)₂— | —CH₂—CH₂—O—CH₂—CH₂— | C₆H₅—CH₂— | Br | 130–134 |
| 93 | 4-C(CH₃)₃ | —CH₃ | —CH₃ | —(CH₂)₂— | —CH₂—CH(CH₃)—O—CH(CH₃)—CH₂— | C₆H₅—CH₂— | Br | resin |
| 94 | 4-C(CH₃)₃ | —CH₃ | —CH₃ | —(CH₂)₂— | —CH₂—CH(CH₃)—O—CH(CH₃)—CH₂— | 4-ClC₆H₄—CH₂— | Br | resin |
| 95 | 4-C(CH₃)₃ | —CH₃ | —CH₃ | —(CH₂)₂— | —CH₂—CH₂—O—CH₂—CH₂— | 4-ClC₆H₄—CH₂— | Br | 126–133 |
| 96 | H | —CH₃ | —CH₃ | —(CH₂)₂— | —CH₂—CH₂—O—CH₂—CH₂— | 4-(tert.-C₄H₉)C₆H₄—CH₂— | Br | 145–148 |
| 97 | 4-C(CH₃)₃ | —CH₃ | —CH₃ | —(CH₂)₂— | —CH₂—CH₂—O—CH₂—CH₂— | 4-(tert.-C₄H₉)C₆H₄—CH₂— | Br | 120 (decomposition) |
| 98 | 4-C(CH₃)₃ | —CH₃ | —CH₃ | —(CH₂)₂— | —CH₂—CH(CH₃)—O—CH(CH₃)—CH₂— | 4-(tert.-C₄H₉)C₆H₄—CH₂— | Br | resin |

The active ingredients have a strong action on microorganisms. They are especially suitable for preventing and curing plant diseases caused by fungi, e.g., Botrytis cinerea in grapes and strawberries, Monilia fructigena in apples, Phytophthora infestans in potatoes and tomatoes, Plasmopara viticola in grapes, and Alternaria solani in tomatoes.

The fungicidal or bactericidal agents contain from 0.1 to 95, and preferably from 0.5 to 90, wt% of active ingredient. Depending on the type of effect desired, the application rates are from 0.1 to 5 kg of active ingredient per hectare.

The imidazolium salts according to the invention are also suitable for industrial purposes, e.g., as wood preservatives. The compounds have also been found to have not only a fungicidal action, but also a bactericidal action—they are also suitable as such for use in crop protection and as industrial microbicides; they are also suitable for external use in human and veterinary medicine. For instance the following microorganisms may be combated:

*Staphylococcus aureus, Escherichia coli, Klebsiella pneumoniae, Citrobacter freundii, Proteus vulgaris, Pseudomonas aeruginosa, Pseudomonas fluorescens, Xanthomonas vesicatoria, Xanthomonas malvaccarum, Erwinia carotovora, Erwinia amylovora, Desulfovibrio desulfuricans, Streptoverticillium rubrireticuli, Aspergillus niger, Aspergillus versicolor, Penicillium funiculosum, Paecilomyces variotii, Trichoderma viride, Chaetomium globosum, Candida albicans, Geotrichum candidans, Monilia sitophila, Scenedesmus quadricauda, Chlorella vulgaris* and *Nostoc muscorum*.

The usual use concentrations are from 0.01 to 1% of active ingredient, based on the weight of the material to be protected; when the active ingredients are used for water treatment in oil production, in swimming baths, cooling towers, air humidifying units, flower preservatives or in the paper industry, amounts of from 5 to 100 ppm are sufficient to suppress microorganism development. Ready-to-use disinfectant solutions contain from 0.2 to 5% of active ingredient.

The agents according to the invention may also be mixed and applied with other active ingredients, e.g., herbicides, insecticides, growth regulators, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together.

Examples of fungicides which may be combined with the compounds according to the invention are: sulfur, dithiocarbamates and their derivatives, e.g. iron(III) dimethyldithiocarbamate, zinc dimethyldithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis-(thiocarbamoyl)-disulfide, zinc N,N'-propylene-bis-dithiocarbamate, and the ammonia complex of zinc N,N'-propylene-bis-dithiocarbamate and N-N'-polypropylene-bis-(thiocarbamoyl)-disulfide;

nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-(1,1,2,2-tetrachloroethylthio)-tetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylaminio)-phosphinyl)-3-phenyl-1,2,4-triazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isozazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, D,L-methyl-N-(2,6-dimethylphenyl)-N-furoyl(2)-alanate, methyl D,L-N-(2,6-dimethylphenyl)-N-(2'-methoxyacetyl)-alanate, diisopropyl 5-nitroisophthalate, 1-(1',2',4'-triazolyl-1')-[1-(4'-chlorophenoxy)]-3,3-dimethylbutan-2-one, 1-(1',2',4'-triazolyl-1')-[1-(4'-chlorophenoxy)]-3,3-dimethylbutan-2-ol, N-(2,6-dimethylphenyl)-N-chloroacetyl-D,L-2-aminobutyrolactone, N-(n-propyl)-N-(2,4,6-trichlorophenoxyethyl)-N'-imidazolylurea, N-cyclohexyl-N-methoxy-2,5-dimethyl-furan-3-carboxamide, 2,4,5-trimethyl-furan-3-carboxanilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, N-[3-(p-tert.-butylphenyl)-2-methyl-propyl]-cis-2,6-dimethylmorpholine, N-formyl-N-morpholine-2,2,2-trichloroethylacetal, 1-[2-(2,4-dichlorophenyl)-4-ethyl-1,3-dioxolan-2-yl-methyl]-1H-1,2,4-triazole, and 1-[2-(2,4-dichlorophenyl)-4-n-propyl-1,3-dioxolan-2-yl-methyl]-1H-1,2,4-triazole.

The active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol ethers, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such formulations are given below.

I. 90 parts by weight of compound 14 is mixed with 10 parts by weight of N-methyl-alpha-pyrrolidone. A mixture is obtained which is suitable for application in the form of very fine drops.

II. 20 parts by weight of compound 15 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 56 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into water and finely distributing it therein, an aqueous dispersion is obtained.

IV. 20 parts by weight of compound 57 is dissolved in a mixuture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound 63 is well mixed with 3 parts by weight of the sodium salt of diisobutyl-naphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 5 parts by weight of compound 68 is intimately mixed with 95 parts by weight of particulate kaolin. A dust is obtained containing 5% by weight of the active ingredient.

VII. 30 parts by weight of compound 69 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 73 is intimately mixed with 10 parts of the sodium salt of a phenolsulfonic acid-urea-formaldehyde condensate, 2 parts of silica gel and 48 parts of water to give a stable aqueous dispersion.

IX. 20 parts of a compound 76 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds. The prior art agent used for comparison purposes was N-trichloromethylthiotetrahydrophthalimide (A).

EXPERIMENT 1

Action on Botrytis cinerea

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results of this experiment show that for example active ingredients nos. 1, 2, 9, 12, 13, 14, 15, 16, 17, 18, 20, 21, 22, 23, 24, 25, 26, 27, 28, 29, 30, 31, 32, 33, 34, 35, 36, 37, 40, 46, 50, 58, 63, 64, 65, 66, 68, 69, 70, 75, 78 and 97 applied as 0.05% spray liquors, had a better action (e.g., 100%) than prior art compound A (e.g., 70%).

EXPERIMENT 2

Action of Phytophthora infestans

Leaves of potted tomatoes of the "Große Fleischtomate" variety were sprayed with aqueous liquors containing (dry basis) 80% of active ingredient and 20% of emulsifier. After the sprayed-on layer had dried, the leaves were infected with a zoospore suspension of Phytophthora infestans. The plants were then placed for 5 days in a steam-saturated chamber kept at 16° to 18° C. After this period, the disease had spread on the untreated control plants to such an extent that the fungicidal action of the compounds was able to be assessed.

The results of the experiment show that for example active ingredients nos. 2, 31, 33, 34, 35, 40, 46, 57, 59, 60, 63, 65, 66, 68, 69, 73, 75 and 78, applied as 0.025% spray liquors, had a better action (e.g., 97%) than compound A (e.g., 60%).

EXPERIMENT 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a steam-saturated (moist) chamber at 24° C., and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of this experiment revealed that for instance active ingredients nos. 40, 46, 59, 60, 63, 68, 69, 75 and 78, applied as 0.25% spray liquors, had a good fungicidal action (e.g., 90%).

EXPERIMENT 4

Action on Aspergillus niger

To determine the action on fungi, the active ingredients are added, in amounts of 100, 50, 25 and 10 parts per million parts of solution, to a nutrient solution ideally suited for promoting the growth of the fungus *Aspergillus niger*. 20 ml of the mixture of nutrient solution and active ingredient was introduced into 100 ml test tubes and inoculated with 0.3 mg of Aspergillus spores. After the flasks had been incubated at 36° C. for 120 hours, the extent of fungus spread (predominantly on the surface of the nutrient solution) was assessed.

The results of this experiment show that for instance active ingredients nos. 1, 14, 15, 22, 28, 82 and 83, applied for example in amounts of 100, 50, 25 and 10 parts per million parts of nutrient solution, had a good action (e.g., 100%).

EXPERIMENT 5

Action on Staphylococcus aureus

To determine the action of the novel compounds on bacteria, 5 ml of increasing dilutions of the active ingredients was added to 5 ml of doubly concentrated nutrient broth in sterile test tubes, and mixed. The tubes were then inoculated by adding one dropl of a 16-hour old broth culture (diluted 1:10) of the bacteria species *Staphylococcus aureus*, and incubated for 24 hours at 37° C. After this time, samples were transferred from the tubes to bacteria nutrient media which were then also incubated for 24 hours at 37° C.

These results show that for instance active ingredients nos. 14, 15, 22, 25, 28, 32, 33, 34, 40, 41, 58, 59, 60, 63, 64, 66, 67, 70, 74, 77, 79, 81, 82, 83 and 97, applied at a dilution rate of 1:10,000 (100 ppm), had a good action (e.g., 100%).

We claim:

1. A diamine derivative of the formula

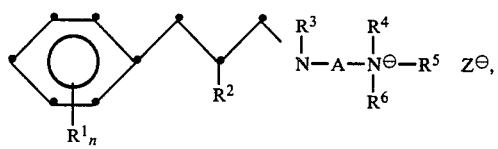

wherein
$R^1$ is unsubstituted or halogen-substituted $C_4$-$C_8$ tertiary alkyl when n=1, or $C_4$-$C_8$ tertiary alkyl and halogen when n=2,
$R^2$ is $C_1$-$C_3$ alkyl,
A is $C_2$-$C_4$ alkylene which is unsubstituted or substituted by $C_1$-$C_3$ alkyl or is $C_5$-$C_7$ cycloalkylene which is unsubstituted or substituted by $C_1$-$C_3$ alkyl,
$R^3$ is $C_1$-$C_2$ alkyl,
$R^4$ and $R^5$ independently of one another are each unsubstituted or halogen substituted $C_1$-$C_3$ alkyl,
$C_3$-$C_5$ alkenyl, propargyl or benzyl which is unsubstituted or substituted by $C_1$-$C_4$ alkyl or halogen, or
$R^3$ and $R^4$ together with A and the two nitrogen atoms which are bonded to A, form an unsubstituted or $C_1$-$C_2$ alkyl-substituted piperazine ring,
$R_6$ is $C_1$-$C_8$ alkyl $C_3$-$C_5$ alkenyl propargyl, unsubstituted, halogen or $C_1$-$C_4$ alkyl mono- to trisubstituted benzyl, phenylethyl or unsubstituted or halogen or $C_1$-$C_4$ alkyl mono- to trisubstituted phenoxyethyl, 4(tert-butyl) phenyl isobutyl, or phenylpropenyl, and
Z is an anion of any non-phytotoxic acid, with the proviso that not more than 2 of $R^4$, $R^5$ and $R^6$ are methyl.

2. A diamine derivative according to claim 1 wherein
$R^1$ is unsubstituted $C_4$-$C_8$ tertiary alkyl, n is 1,
$R^2$ is $C_1$-$C_3$ alkyl,
$R^3$ and $R^4$, together with A and the two nitrogen atoms which are bonded to A, form an unsubstituted or $C_1$-$C_2$ alkyl substituted piperazine ring,
$R^5$ is halogen-substituted benzyl,
$R^6$ is $C_1$-$C_8$ alkyl, and
Z is an anion of any non-phytotoxic acid.

3. A diamine derivative according to claim 1 wherein
$R^1$ is unsubstituted $C_4$-$C_8$ tertiary alkyl,
n is 1,
$R^2$ is $C_1$-$C_3$ alkyl,
$R^3$ and $R^4$, together with A and the two nitrogen atoms which are bonded to A, form an unsubstituted or $C_1$-$C_2$ alkyl substituted piperazine ring
$R^5$ is benzyl or $C_1$-$C_4$ alkyl substituted benzyl,
$R^6$ is $C_1$-$C_8$ alkyl, and
Z is an anion of any non-phytotoxic acid.

4. A diamine derivative of the formula I as set forth in claim 14, wherein $R^1$ is t-butyl.

5. The compound of the formula I of claim 1 which is

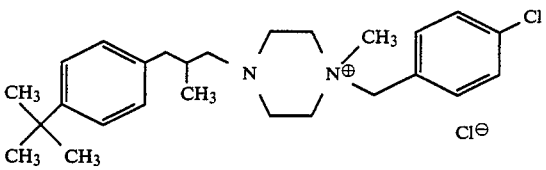

6. A fungicidal and/or bactericidal agent which comprises: an inert carrier and from 0.1 to 95% by weight of a diamine as defined in claim 1.

7. A fungicidal agent which comprises: an inert carrier and from 0.1 to 95% by weight of a diamine as defined in claim 4.

8. A process for combating fungi, wherein a diamine of the formula I as claimed in claim 1 is allowed to act on the areas, materials, plants or seed threatened by fungus attack.

9. A process for combating bacteria, wherein a diamine of the formula I of claim 1 is allowed to act on the areas threatened by bacterial attack.

* * * * *

UNITED STATES PATENT AND TRADEMARK OFFICE
CERTIFICATE OF CORRECTION

PATENT NO. : 4,599,335

DATED : July 8, 1986

INVENTOR(S) : Rentzea et al

It is certified that error appears in the above-identified patent and that said Letters Patent is hereby corrected as shown below:

Column 22, line 37, "claim 14" should read -- claim 1 --.

Signed and Sealed this

Seventeenth Day of March, 1987

Attest:

DONALD J. QUIGG

Attesting Officer

Commissioner of Patents and Trademarks